US012649685B2

(12) United States Patent　　　　　(10) Patent No.:　US 12,649,685 B2
Grimm et al.　　　　　　　　　　　　　(45) Date of Patent:　　Jun. 9, 2026

(54) METHOD FOR ERADICATING PATHOGENS

(71) Applicant: Schott AG, Mainz (DE)

(72) Inventors: Malte Grimm, Mitterteich (DE);
Rainer Eichholz, Frankfurt am Main
(DE); Josef Rasp, Waldsassen (DE);
Andre Petershans, Nabburg (DE);
Klaus Megges, Weiden (DE); **Susanne
Krüger, Mainz (DE); Thomas Pfeiffer**,
Ingelheim (DE)

(73) Assignee: SCHOTT AG, Mainz (DE)

( * ) Notice: Subject to any disclaimer, the term of this
patent is extended or adjusted under 35
U.S.C. 154(b) by 1223 days.

(21) Appl. No.: 17/541,759

(22) Filed: Dec. 3, 2021

(65) Prior Publication Data

US 2022/0177354 A1　　Jun. 9, 2022

(30) Foreign Application Priority Data

Dec. 3, 2020　(EP) ..................................... 20211687
Dec. 23, 2020　(DE) .................... 20 2020 107 535.7
May 21, 2021　(EP) ..................................... 21175361
Aug. 17, 2021　(EP) ..................................... 21191643

(51) Int. Cl.
　*C03C 3/118*　　　　(2006.01)
　*A61L 2/10*　　　　(2006.01)
　(Continued)

(52) U.S. Cl.
　CPC ................ *C03C 3/118* (2013.01); *A61L 2/10*
　(2013.01); *A61L 2/26* (2013.01); *C03C 3/089*
　(2013.01); *C03C 3/091* (2013.01); *C03C 3/093*
　(2013.01); *C03C 3/115* (2013.01); *C03C*
　*4/0085* (2013.01); *A61L 2202/11* (2013.01);
　*C03C 2204/00* (2013.01)

(58) Field of Classification Search
　CPC .......... C03C 4/0085; C03C 3/118; C03C 3/91
　See application file for complete search history.

(56) References Cited

U.S. PATENT DOCUMENTS 3,994,708 A * 11/1976 VON Reth ........... C03C 4/0085
　　　　　　　　　　　　　　　　　　　65/32.5
5,045,509 A　　9/1991 Kiefer
　　　　　　　　　(Continued)

FOREIGN PATENT DOCUMENTS

CN　　110240402 A　　9/2019
CN　　112209617 A　　1/2021
　　　　　　　(Continued)

OTHER PUBLICATIONS

Qiu. Machine translation of CN-112209617A. Published Jan. 12,
2021. Translated on Oct. 18, 2025 using PE2E (Year: 2021).*
(Continued)

*Primary Examiner* — Matthew E. Hoban
(74) *Attorney, Agent, or Firm* — TAYLOR &
EDELSTEIN, PC

(57)　　　　　　ABSTRACT

A glass has a transmittance at a wavelength of 220 nm of at
least 30% and a transmittance at a wavelength of 200 nm of
less than 4.0%, the glass having a total platinum content of
less than 3.5 ppm. A device and a sterilizer include a light
source configured to output ultraviolet light and a lamp
cover covering the light source and including the glass.

22 Claims, 4 Drawing Sheets

(51) Int. Cl.
| | |
|---|---|
| *A61L 2/26* | (2006.01) |
| *C03C 3/089* | (2006.01) |
| *C03C 3/091* | (2006.01) |
| *C03C 3/093* | (2006.01) |
| *C03C 3/115* | (2006.01) |
| *C03C 4/00* | (2006.01) |

(56) References Cited

U.S. PATENT DOCUMENTS

| | | | |
|---|---|---|---|
| 9,145,333 B1* | 9/2015 | Dejneka | C03C 3/091 |
| 9,381,458 B2 | 7/2016 | Blechschmidt et al. | |
| 10,910,210 B2 | 2/2021 | Yagyu et al. | |
| 11,167,051 B2 | 11/2021 | Randers-Pehrson et al. | |
| 2005/0013729 A1 | 1/2005 | Brown-Skrobot et al. | |
| 2005/0096545 A1 | 5/2005 | Haider et al. | |
| 2009/0075805 A1 | 3/2009 | Kurachi et al. | |
| 2013/0236353 A1* | 9/2013 | Blechschmidt | C02F 1/325 |
| | | | 422/4 |
| 2018/0057393 A1 | 3/2018 | Sakagami et al. | |
| 2019/0321499 A1* | 10/2019 | Igarashi | A61L 2/26 |
| 2019/0352217 A1* | 11/2019 | Lautenschläger | C03C 3/091 |
| 2022/0177352 A1 | 6/2022 | Petershans et al. | |

FOREIGN PATENT DOCUMENTS

| | | |
|---|---|---|
| DE | 33 20 980 C2 | 1/1987 |
| DE | 10 2009 021 115 A1 | 11/2010 |
| DE | 20 2020 107 535 U1 | 6/2021 |
| EP | 1 101 740 A1 | 5/2001 |
| JP | 60-46946 A | 3/1985 |
| JP | 62-87433 | 4/1987 |
| JP | 2-141438 U | 11/1998 |
| JP | 2001064038 A | 3/2001 |
| JP | 2011-32162 A | 2/2011 |
| WO | 2008/029799 A1 | 3/2008 |
| WO | 2017163963 A1 | 9/2017 |

OTHER PUBLICATIONS

1 English translation of German Patent No. 33 20 980 C2 issued Jan. 15, 1987 (3 pages).

Translation of Japanese Office Action dated Aug. 16, 2022 for Japanese Patent Application No. 2021-135578 (7 pages).

European Communication Pursuant to Article 94(3) EPC dated May 23, 2022 for European Patent Application No. 21191643.2 (14 pages).

European Search Report dated May 13, 2022 for European Patent Application No. 21191643.2 (8 pages).

Kouji Narita et al., "Disinfection and healing effects of 222-nm UVC light on methicillin-resistant *Staphylococcus aureus* infection in mouse wounds" Journal of Photochemistry & Photobiology, B: Biology, Elsevier Science S.A., Basel, CH, vol. 178, pp. 10-18, Oct. 27, 2017 (10 pages).

Yuki Kaiki MD, et al., "Methicillin-resistant *Staphylococcus aureus* contamination of hospital-use-only mobile phones and efficacy of 222-nm ultraviolet disinfection", American Journal of Infection Control, vol. 000, pp. 1-4, Nov. 10, 2020 (4 pages).

European Search Report dated Jul. 8, 2021 for European Patent Application No. 20211687.7 (8 pages).

Partial European Search Report dated Jan. 31, 2022 for European Patent Application No. 21 19 1643 (14 pages).

Extended European Search Report Dated Jan. 21, 2022 for European Patent Application No. 21175361.1 (8 pages).

\* cited by examiner

METHOD FOR ERADICATING PATHOGENS

CROSS REFERENCE TO RELATED APPLICATIONS

This application claims priority to European Patent Application No. EP 21191643.2 filed on Aug. 17, 2021, European Patent Application No. EP 21175361.1 filed on May 21, 2021, and European Patent Application No. EP 20211687.7 filed on Dec. 3, 2020, which are all incorporated in their entirety herein by reference. This application also claims priority to German Patent Application No. DE 20 2020 107 535.7 filed on Dec. 23, 2020, which is incorporated in its entirety herein by reference.

BACKGROUND OF THE INVENTION

1. Field of the Invention

The present invention relates to methods for eradication of pathogens, especially to methods for eradicating bacteria in confined spaces.

2. Description of the Related Art

The most relevant pathogens are bacteria and viruses. Pathogens pose a constant threat for humans and livestock. Many methods for elimination of pathogens were developed, including elimination with light. The current SARS-CoV2 pandemic increased the need for effective and specific ways of pathogen elimination, particularly virus elimination.

Pathogens may become a major problem in hospitals, prisons, and nursing homes, where people with open wounds, invasive devices such as catheters, and weakened immune systems are at a greater risk of infection. Regular disinfection and antibiotic/antiviral agents are possible ways to address these threats. However, disinfectants may be very aggressive and cause irritant fumes that may cause harm themselves or reduce the desire to use these agents effectively, particularly in confined spaces. Antibiotics/antiviral agents may lead to resistances in the pathogens, rendering the agents largely ineffective.

Thus, there is a great need of easy-to-use and effective eradication methods against pathogens, especially bacteria and viruses in confined spaces such as hospitals, schools and nursing homes.

Methods for eradication of pathogens by light have been reported in the art. The so called "photosensitizer-method" is used widely in hospitals and other areas with elevated pathogen-risks (or other bacterial contaminations). This method makes use of photosensitizers, mostly dye molecules, that become excited when illuminated with light. When excited by light, these molecules produce reactive oxygen species, which then eradicate the pathogens.

However, not all reported methods using photosensitizers are sufficient to eradicate enough microorganisms to effectively prevent infections. This is because photosensitizers may not be concentrated enough to do significant damage. In addition, many photosensitizers are hydrophobic. This makes it difficult to disperse them in aqueous environments, where microorganisms typically exist (e.g. biofilms).

Another method in the art is called "ultraviolet germicidal irradiation" (UVGI), that uses short-wavelength ultraviolet (UVC) light to kill or inactivate microorganisms by destroying nucleic acids and disrupting their DNA, leaving them unable to perform vital cellular functions. UVGI is used in a variety of applications, such as food, air, and water purification.

UVGI devices can produce strong enough UVC light in circulating air or water systems to make them inhospitable environments to microorganisms such as bacteria, viruses, molds and other pathogens. UVGI can be coupled with a filtration system to sanitize air and water. The application of UVGI to disinfection has been an accepted practice since the mid-20th century. It has been used primarily in medical sanitation and sterile work facilities.

Increasingly, it has been employed to sterilize drinking and wastewater, as the holding facilities are enclosed and can be circulated to ensure a higher exposure to the UV. In recent years UVGI has found renewed application in air purifiers.

However, it has been reported that conventional germicidal UV lamps are harmful for the eye, produce pre-mutagenic UV-associated DNA lesions in human skin and are cytotoxic to exposed mammalian skin.

Thus, the danger of damaging effects, including even the induction of cancer or other mutagenic diseases, prevent the direct use of common UVGI-methods for eradication of pathogens on mammalian skin, such as for example the skin of patients, health care personnel or livestock.

It has been recently reported that far-UVC-light kills bacteria efficiently regardless of their drug-resistant proficiency, but without the skin- or eye-damaging effects associated with conventional germicidal UV exposure.

However, UV-absorption of UV-light at wavelengths of about 200 nm to about 250 nm is very high in otherwise transparent covers. For example, UV-light does not transmit well through conventional glasses at wavelengths beyond 320 nm. Conventional glasses do not transmit light at wavelengths below 290 nm. Thus, these covers have the disadvantage that they are either impermissible for far-UV-light, or at least a high amount of energy is necessary to guarantee a sufficient UV-exposure of the treated surface, e.g. the treated skin.

SUMMARY OF THE INVENTION

In some exemplary embodiments provided according to the present invention, a glass has a transmittance at a wavelength of 220 nm of at least 30% and a transmittance at a wavelength of 200 nm of less than 4.0%. The glass has a total platinum content of less than 3.5 ppm.

In some exemplary embodiments provided according to the present invention, a device includes a light source configured to output ultraviolet (UV) light and a lamp cover covering the light source. The lamp cover includes a glass having a transmittance at a wavelength of 220 nm of at least 30% and a transmittance at a wavelength of 200 nm of less than 4.0%. The glass has a total platinum content of less than 3.5 ppm.

In some exemplary embodiments provided according to the present invention, a sterilizer includes a light source configured to output ultraviolet (UV) light at a wavelength of 222 nm and a lamp cover covering the light source. The lamp cover includes a glass having a transmittance at a wavelength of 220 nm of at least 30% and a transmittance at a wavelength of 200 nm of less than 4.0%. The glass has a total platinum content of less than 3.5 ppm.

BRIEF DESCRIPTION OF THE DRAWINGS

The above-mentioned and other features and advantages of this invention, and the manner of attaining them, will become more apparent and the invention will be better understood by reference to the following description of embodiments of the invention taken in conjunction with the accompanying drawings, wherein.

Corresponding reference characters indicate corresponding parts throughout the several views. The exemplifications set out herein illustrate embodiments of the invention and such exemplifications are not to be construed as limiting the scope of the invention in any manner.

DETAILED DESCRIPTION OF THE INVENTION

Figures 1A, 1B, 1C, 1D, 1E, 1F:
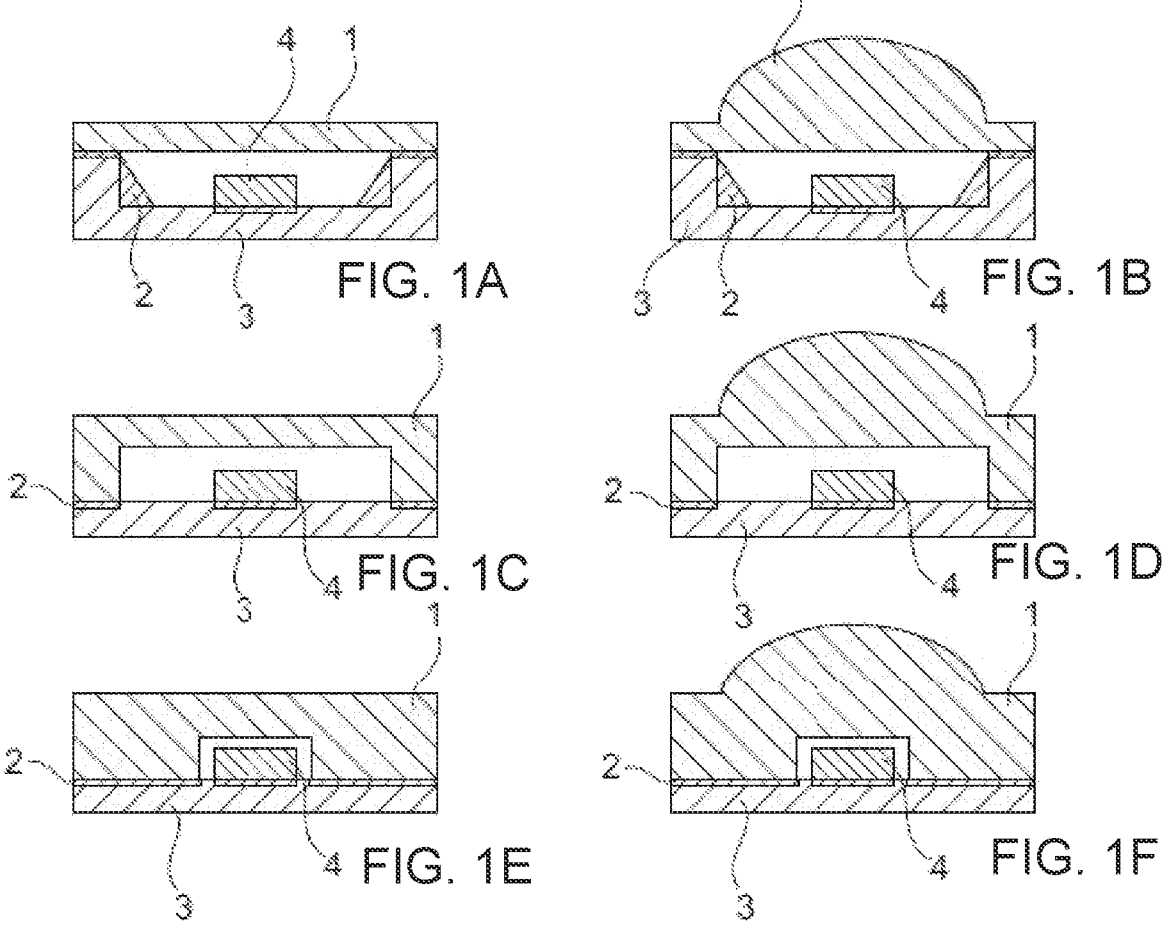
FIGS. 1A to 1F illustrate potential uses of UV-transparent glasses provided according to the present invention in different LED-packages.
Figures 2A, 2B, 2C, 2D, 2E:
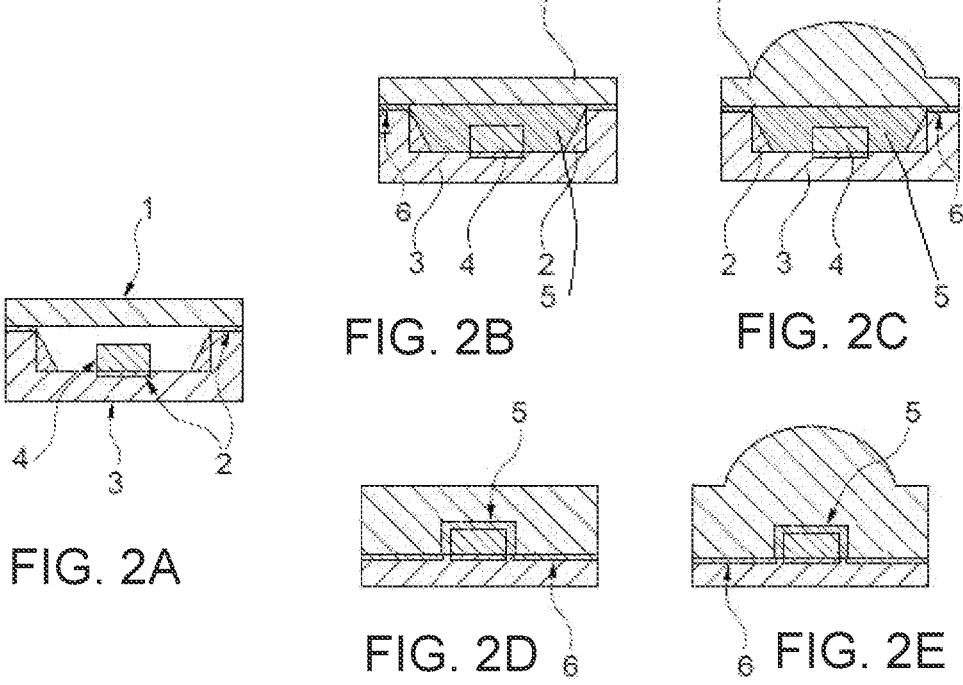
FIGS. 2A to 2E illustrate how the UV-transparent glasses provided according to the present invention may be attached to a casing via laser frit sealing.

In some embodiments, the invention pertains to a method for eradicating pathogens, the method comprising exposing the pathogens to germicidal UV light at a wavelength of 222 nm, wherein the UV light is irradiated by a UV lamp having a lamp cover made of a glass, the glass having a transmittance of at least 30% at a wavelength of 220 nm and less than 4% at 200 nm. Optionally, the concentration of ozone may be less than 0.12 mg/m$^3$ in the room where the method is carried out.

The lamp cover, being disposed between the light source and the space to be irradiated, has a minimum transmission for UV light at 220 nm so that sufficient 220 nm-UV light intensity reaches the space to be treated. At 220 nm many pathogens are particularly vulnerable to light irradiation whereas the human eyes and skin are less sensitive. Additionally, the light transmittance of the lamp cover is very low at 200 nm. Reducing the light intensity at about 200 nm limits the photolysis rate caused by UV irradiation. Photolysis causes formation of ozone. Ozone may be a problem in confined spaces, e.g. homes and offices, when present in concentrations of more than 0.12 mg/m$^3$. The method disclosed herein reduces ozone formation while safeguarding sufficient elimination of pathogens.

In some embodiments, the invention relates to a method for eradicating pathogens, the method comprising exposing the pathogens to germicidal UV light at a wavelength of 220 nm, wherein the UV light is irradiated by a UV lamp having a lamp cover made of a glass, the glass having a total platinum content of less than 3.5 ppm.

UV radiation is able to split organic bonds. As a result, it is hostile to life by destroying biogenic substances. In addition, many plastics are damaged by ultraviolet radiation due to haze, embrittlement, and/or decay. At lower wavelength, UV-light causes photolysis which leads to increased ozone concentrations in the surrounding air.

In humans, excessive exposure to UV radiation can result in acute and chronic harmful effects on the eye's dioptric system and retina. The skin, the circadian and immune systems can also be affected. The skin and eyes are most sensitive to damage by UV at 265 to 275 nm.

Thus, the wavelengths, which are applied according to the method disclosed herein, include 220 nm. Ultraviolet (UV) light of about 220 nm has similar antimicrobial properties as typical germicidal UV light (254 nm), but without inducing damage to outer tissue coverings of higher animals, such as amphibian, reptile, bird, mammal or human skin.

The limited penetration distance of 220 nm light in biological samples (e.g. stratum corneum) compared with that of 254 nm light allows for the selective antimicrobial treatment without harming mammalian or human skin, such as the skin of a patient or health care professional.

Considering the eye, the most important target from the perspective of UV risk is the lens. The lens is located distal to the cornea, which is sufficiently thick (500 μm) such that penetration of 220 nm light through the cornea to the lens is low. Even if one considers effects on the cornea from the perspective of photokeratitis, any protective device against eye splash, which is now almost universal amongst surgical staff, would be expected to sufficiently protect the cornea from 220 nm UV exposure.

At the cellular level, bacteria are much smaller than almost any human cell. Typical bacterial cells are less than 1 μm in diameter, whereas typical eukaryotic cells range in diameter from about 10 to 25 μm. It follows, that 220 nm UV light can penetrate throughout typical bacteria-cells but cannot penetrate significantly beyond the outer perimeter of the cytoplasm of typical eukaryotic cells, such as human cells, and will be drastically attenuated before reaching the eukaryotic cell nucleus.

By contrast, higher wavelength light from a conventional germicidal lamp can reach human cell nuclei without major attenuation. Based on these biophysical considerations, while radiation from a conventional UVC lamp is cytotoxic and mutagenic to both bacteria and human cells, 220 nm UV light is cytotoxic to bacteria, but much less cytotoxic or mutagenic to human cells.

UV-light of wavelengths at 200 nm and below, however, are not useful, because at these wavelengths a sufficient eradication of pathogens cannot be reached anymore. Furthermore, at wavelengths of 200 nm and below, UV reacts with oxygen and forms ozone, an effect which is not desired.

The UVC light at about 222 nm efficiently eradicates pathogens regardless of their drug-resistant proficiency, but without the skin and eye damaging effects associated with conventional germicidal UV exposure.

The term "eradication" is used herein for any reduction of pathogens after treatment of more than 90%, more than 95%, more than 99%, more than 99.9%, or more than 99.99% according to ISO 22196:2011-08-31.

In order to achieve such an eradication, in some embodiments the invention pertains to a method wherein the UV-exposure of the pathogen and/or the surface to be treated is in the range from 2,000 to 8,000 μW·s/cm$^2$, from 2,100 to 7,000 μW·s/cm$^2$, from 2,200 to 5,000 μW·s/cm$^2$, or from 2,300 to 3,000 μW·s/cm$^2$. In some embodiments, the UV-exposure of at least about 2,500 μW·s/cm$^2$ results in a 90% reduction of at least one pathogen.

The methods provided according to the present invention can be used for eradicating pathogens in confined spaces, e.g. homes, hospitals, schools, or nursing homes. The reduced production of ozone and limited potential to harm human health makes this method ideal for regular or even continuous use. Optionally, the method can be used to eliminate pathogens on UV-sensitive material, such as UV-sensitive surfaces.

In some embodiments, the UV-sensitive material may be susceptible to crosslinking of monomers to produce specific polymers by UV-radiation above 250 nm and/or up to 295 nm. In some embodiments, the UV-sensitive material may be a gas or a liquid, which is sensitive to UV above 250 nm and/or up to 295 nm.

In some embodiments, the UV-sensitive material may be a pharmaceutical composition, which is sensitive to UV above 250 nm and/or up to 295 nm.

In some embodiments, the UV-sensitive material may be a biological tissue surface, such as a skin of an insect, invertebrate, vertebrate, mammal or human, (e.g. mollusc, fish, amphibia, reptile, bird, mammal and/or human or a chitinous exoskeleton from an arthropod, such as a lobster or an insect).

Thus, the term "biological tissue surface" according to the definition of this invention encompasses all biological surfaces, which may be harmed by UV-radiation above 250 nm and/or up to 295 nm. In some embodiments, the invention includes biological surfaces which may be harmed by UV-radiation outside the wavelength range of 207 to 220 nm, and which are not harmed by UV-radiation at the wavelength of about 220 nm.

Within this invention the term "tissue" is used for any cellular organizational level between cells and a complete organ. A tissue is an ensemble of similar cells and their extracellular matrix from the same origin that together carry out a specific function. Organs are then formed by the functional grouping together of multiple tissues.

Of course, especially tissue which may be exposed to UV-radiation during pathogen eradication method should be encompassed. In most of the cases, those tissues will be epithelial tissues that are formed by cells that cover the organ surfaces, such as the surface of skin, the airways, the reproductive tract, and the inner lining of the digestive tract. The cells comprising an epithelial layer are linked via semi-permeable, tight junctions; hence, this tissue provides a barrier between the external environment and the organ it covers. In addition to this protective function, epithelial tissue may also be specialized to function in secretion, excretion and absorption. Epithelial tissue helps to protect organs from microorganisms, injury, and fluid loss.

Thus, methods provided according to the present invention include those methods where conventional UVGI-methods may not be applicable or suitable, such as for example UV-treatment of pathogens residing on a UV-sensitive surface, such as for example skin tissue or where eye exposure to UV cannot be avoided.

The term "mammal" refers herein to any vertebrate animal constituting the class Mammalia and characterized by the presence of mammary glands which in females produce milk for feeding (nursing) their young, a neocortex (a region of the brain), fur or hair, and three middle ear bones. These characteristics distinguish them from reptiles and birds, from which they diverged in the late Triassic, 201-227 million years ago. There are around 5,450 species of mammals. The largest orders are the rodents, bats and Soricomorpha (shrews and others). The next three are the Primates (apes, monkeys, and others), the Cetartiodactyla (cetaceans and even-toed ungulates), and the Carnivora (cats, dogs, seals, and others). This definition of mammals also includes humans.

Thus, the term "mammal skin" refers to any skin of a mammal, including the skin of livestock, wherein the term "livestock" is commonly defined as domesticated animals raised in an agricultural setting to produce labor and commodities such as meat, eggs, milk, fur, leather, and wool, such as for example cattle, goats, horses, pigs and sheep.

Furthermore, the term "mammal skin" includes also the skin of humans, such as for example patients, health care professionals, people with weak or absent immune-system (elderly, children, post-surgery, post organ transplantation, HIV-positive, etc.), people with elevated potential exposure to pathogens, etc.

Prior art UV lamp covers are made of sapphire, synthetic quartz or quartz glass (fused silica glass). However, sapphire is very expensive as compared to other transparent materials and cannot be bent, molded, drawn or melt-fused like glasses or metals. In addition, the UV-absorption at UVC wavelengths is quite high with nearly no transmission at wavelengths below 250 nm.

In some embodiments, the glass has a transmittance of at least 30%, at least 35%, at least 40% or at least 60% at 220 nm and/or at least 75% at wavelengths [$\lambda$] of 260 nm, 280 nm and/or 310 nm (measured at a thickness of 0.71 mm).

Quartz and fused silica glasses, due to their high melting point, have high fabrication costs, since temperature and effort for melting and forming are much higher than for other glasses. Furthermore, any forms other than tubes or sheets must be ground and polished from blocks or ingots. Besides the costs of production, these covers have the disadvantage that high amounts of energy are necessary to guarantee a sufficient UV-exposure of the treated object, gas or liquid.

The glasses disclosed herein, however, are suitable for forming rods, tubes, sheets and bars, produced by casting, Danner, Vello, redraw and/or down-draw processes.

The glasses provided according to the present invention may have excellent optical properties. In some embodiments, the glass has a refractive index $n_d$ ($\lambda$=587.6 nm) of 1.48 to 1.58. The refractive index can be 1.50 or more.

The glass described herein has excellent UV transmission at wavelengths significantly above 200 nm. The glass has one or more of the following optical properties:

a UV transmittance at 200 nm of less than 4.0%, in some embodiments less than 3.0%;

a UV transmittance at 220 nm of at least 20%, in some embodiments at least 30%, at least 40%, at least 50% or at least 60%;

a UV transmittance at 240 nm of at least 45%, in some embodiments at least 50%, at least 60%, or at least 70%;

a UV transmittance at 260 nm of at least 65%, in some embodiments at least 70%; or at least 80% and/or a UV transmittance at 280 nm of at least 72.5%, in some embodiments at least 85%.

In some embodiments, the glass has a UV transmittance at 220 nm (measured at a thickness d=0.71 mm) of at least 40%.

Throughout this disclosure, unless otherwise indicated, any reference to a transmittance relates to the transmittance at a reference thickness of 0.71 mm. This does not mean that the glass, glass article or lamp cover has this particular thickness. The thickness serves as a reference for the determination of transmittance. Transmittance can be measured at a different thickness and the result used to calculate the 0.71 mm transmittance value.

The glass and/or the glass article may have a transmittance of at least 50%, for example at least 70%, at least 80%, or at least 83% at a wavelength of 254 nm. In some embodiments, the transmittance at 254 nm is at most 99.9%, at most 95% or at most 90%.

For clarity: The indication that a transmittance is measured at a certain wavelength does not mean that the glass is limited to the indicated thickness. Instead, the thickness indicates the thickness at which the transmittance can be measured. The indication of a thickness for measurement ensures that the values can be compared. The skilled person will understand that glasses of any suitable thickness can be used in the glass covers and devices described hereinunder.

The present invention makes use of and relates to glass and glass covers (lamp covers, LED cover glass) which show low UV-absorption (i.e. high UVC-transmittance) up to a certain wavelength and lower transmittance at lower wavelengths, thereby decreasing the operation energy, reducing the operation temperature and limit photolysis. Furthermore, the glass and glass covers provided according to the present invention are comparably cheap and easy to manufacture, can be bent, molded, drawn or melt-fused to guarantee a manifold of shapes, and are resistant to most chemicals, as well as temperature and physical stress.

In some embodiments, the glass has a transmittance at a wavelength of 220 nm of at least 30% and a transmittance at a wavelength of 200 nm of less than 4.0%, wherein the glass has a total platinum content of not more than 3.5 ppm, in some embodiments also having a low iron and titanium content of less than 10 ppm each.

In some embodiments it has been found that Pt-contaminations (i.e. $Pt^0$, $Pt^{2+}$, $Pt^{4+}$, and $Pt^{6+}$, also referred to as "total platinum content") in the glass may reduce the UV-transmittance between 200 nm and about 250 nm. Without being bound to theory, it is assumed that platinum-contamination in the glass may induce phase-separation by the formation of nuclei within the glass. The glass provided according to the present invention may have none or very low metal contamination, for example Pt-contamination of below 3.5 ppm, or below 2.5 ppm. In some embodiments, the glass may have Pt-contamination of above 0.05 ppm, or above 0.1 ppm. In some embodiments, between 0 and 3.5 ppm, between 0 and 2.5 ppm, between 0 and 2.0 ppm, between 0 and 1.5 ppm, between 0 and 1.0 ppm, between 0 and 0.75 ppm, between 0 and 0.5 ppm, between 0 and 0.25 ppm are provided. In some embodiments, the glass is free of any Pt-contamination.

In some embodiments it has been found that also $TiO_2$ contamination (also referred to as "titanium content") in the glass may further reduce the UV-transmission between 200 nm and about 250 nm. Thus, in some embodiments, glasses with a $TiO_2$ content of 100 ppm or less, for example 50 ppm or less are provided. In some embodiments, the amount of $TiO_2$ should be below 10 ppm, below 7 ppm, below 5 ppm, or below 4 ppm. In some embodiments the $TiO_2$ content may be between 1 and 10 ppm, between 1.5 and 9.0 ppm, between 2.0 and 8.0 ppm, or between 1 and 5 ppm.

In some embodiments, it has been found that also Fe-contamination in the glass may further reduce the UV-transmission between 200 nm and about 250 nm. In this description, iron contents are expressed as parts by weight of $Fe_2O_3$ in ppm. This value can be determined in a manner familiar to the person skilled in the art by determining the amounts of all iron species present in the glass and assuming for the calculation of the mass fraction that all iron is present as $Fe_2O_3$. For example, if 1 mmol of iron is found in the glass, the mass assumed for the calculation corresponds to 159.70 mg $Fe_2O_3$. This procedure takes into account the fact that the quantities of the individual iron species in the glass cannot be determined reliably or only with great effort. In some embodiments the glass contains less than 100 ppm $Fe_2O_3$, for example less than 50 ppm or less than 10 ppm. In some embodiments with a particularly low iron content, the content of $Fe_2O_3$ is less than 10 ppm, less than 8 ppm, or less than 4.5 ppm. Optionally, the $Fe_2O_3$ content is between 0.5 and 10 ppm, between 1 and 10 ppm, between 1.5 and 9.0 ppm, between 2 and 8.5 ppm, between 2.5 and 8.0 ppm, or between 3 and 7 ppm.

It was found that in the glass provided according to the present invention, reducing conditions during the melt may increase the absorption at about 200 nm. Thus, it is desired to choose reducing melting conditions during production of the glass to an extent that leads to a low transmittance at about 200 nm. This can be achieved, for example, by addition of one or more reducing agents, such as sugar (reducing saccharides, e.g. sucrose), during the melt, for example in an amount of from 0.1 to 1.0 wt.-%, for example from 0.2 to 0.6 wt.-%. However, the conditions should not be too reducing in order to avoid high proportions of Fe' species that may have a negative impact on the transmittance at 220 nm.

In some embodiments, the partial pressure of oxygen ($pO_2$) in the glass melt at a temperature of 1500° C. is 0.5 bar or less when the glass melt is produced from the glass by inductively heating to a temperature of 1500° C. in a platinum crucible under argon atmosphere. The $pO_2$ at 1500° C. may for example be at most 0.4 bar, at most 0.3 bar, or at most 0.2 bar. In some embodiments, the $pO_2$ may for example be at least 0.01 bar, at least 0.02 bar, at least 0.05 bar, or at least 0.1 bar. The $pO_2$ may for example be from 0.01 bar to 0.5 bar, from 0.02 bar to 0.4 bar, from 0.05 bar to 0.3 bar, or from 0.1 bar to 0.2 bar.

The $pO_2$ of the glass melt may for example be determined based on the voltage between a reference electrode and a measuring electrode both of which are positioned in the glass melt. The $pO_2$ can be calculated from the voltage between the electrodes by using the Nernst equation. A platinum plate can be used as measuring electrode. The reference electrode may comprise a platinum wire positioned inside a $ZrO_2$ ceramic tube that is closed at the tip, wherein the platinum wire is in electrically conducting contact with the wall of the $ZrO_2$ tube. The $ZrO_2$ ceramic may be yttrium-stabilized, calcium-stabilized, or magnesium-stabilized (see for example EP 1 101 740 A1, par. [0012], [0013]). For the measurement of the $pO_2$ of the glass melt, pure oxygen is flowing around the platinum wire so that there is a constant $pO_2$ of 1.0 bar at the platinum wire inside the reference electrode. The $ZrO_2$ is an oxygen conductor and forms a bridge between the platinum inside the reference electrode and the glass melt, and thus indirectly also with the platinum measuring electrode inside the glass melt. Oxygen ions migrate. The concentration cell "platinum ($pO_2$=constant=1.0 bar)/$ZrO_2$/glass melt/platinum ($pO_2$ of the glass melt)" generates a voltage. The voltage between the reference electrode and the measuring electrode is proportional to the $pO_2$ in the glass melt and can thus be converted to determine the $pO_2$ in the glass melt based on the Nernst equation.

In some embodiments, the content of $Fe_2O_3$ is from 1 ppm to 10 ppm, the amount of $TiO_2$ is from 2 ppm to 30 ppm, and the transmittance at 200 nm is less than 3%.

Thus, in some embodiments glasses are provided with a sum of all contaminations with Pt, $TiO_2$ and/or $Fe_2O_3$ of below 20 ppm, for example below 18.5 ppm, below 13.5 ppm, or below 10.5 ppm. In some embodiments glasses are provided with a sum of all contaminations Pt, $TiO_2$ and/or $Fe_2O_3$ between 1 and 20 ppm, between 1.5 and 18.5 ppm, between 2.0 and 13.5 ppm, or between 2.5 and 12.0 ppm, In some embodiments the glass is free of the contaminations with at least one of the impurities selected from Pt, $TiO_2$ and/or $Fe_2O_3$.

Also other contaminations with transition elements and/or heavy metals such as lead, rhodium, cadmium, mercury and hexavalent chromium may be kept below 10 ppm, for example below 8.5 ppm. In some embodiments these contaminations may be kept between 0 and 8.2 ppm, between 0 and 7.0 ppm, between 0 and 6.0 ppm, between 0 and 5.0 ppm, or between 0 and 4.0 ppm. In some embodiments, the level of these contaminations may be between 0 and 3.0 ppm, between 0 and 2.0 ppm, between 0 and 1.0 ppm, between 0 and 0.5 ppm, or between 0 and 0.25 ppm. In some embodiments, the glass is free of any transition metal and/or heavy metal-contamination.

If a reference is made herein to a chemical element, then this statement refers to any chemical form, unless otherwise stated in the individual case. For example, the statement that the glass has a content of As of less than 100 ppm means that the sum of the mass fractions of the As species present (e.g. $As_2O_3$, $As_2O_5$, etc.) does not exceed the value of 100 ppm.

As used herein, the term "ppm" means parts per million on a weight-by-weight basis (w/w).

Metal contaminations during the production process need to be avoided in order to produce glasses with suitable UV-transmission. Thus, the present invention may also pertain to methods to produce glasses with high UV-transmission.

In some embodiments, the glass provided according to the present invention is a glass with high UV-transmission and the following additional ranges of physical and chemical parameters.

Unlike quartz, the glasses provided according to the present invention have excellent melting properties, e.g. low transformation temperatures and working points. Examples of suitable glass parameters may be selected from a transformation temperature $T_g$ (ISO 7884-8) below 550° C., such as from 400° C. to 500° C., in some embodiments between 440° C. and 480° C.; in some embodiments between 450° C. and 470° C.

The glass may have a Tia temperature, i.e. a glass temperature at a viscosity $\eta$ in dPa*s of $10^{13}$ (annealing point) (ISO 7884-4), between 410° C. and 550° C., such as in some embodiments between 455° C. and 495° C.; in some embodiments between 460° C. and 490° C. The glass may have a softening point, i.e. the temperature at which the viscosity is $10^{7.6}$ dPa*s (softening point) (ISO 7884-3) between 630° C. and 720° C., such as in some embodiments between 640° C. and 700° C., in some embodiments between 650° C. and 690° C. The glass may have a working point, i.e. the temperature at which the viscosity is $10^4$ dPa*s (working point) (ISO 7884-2) between 900° C. and 1150° C., in some embodiments such as between 950° C. and 1100° C.; in some embodiments between 975° C. and 1050° C. The temperature-viscosity dependence expressed by one or more of these parameters goes along with the ability of the glass to be drawn or otherwise formed into any desired shape, including UV lamp covers and UV-LED covers.

The glasses provided according to the present invention may have a density p at 25° C. between 2.3 and 2.7 $g*cm^{-3}$, or between 2.4 and 2.6 $g*cm^{-3}$, e.g. below 2.55 $g*cm^{-3}$. The low density makes the glass most suitable for mobile applications, e.g. mobile pathogen eradication equipment.

The glasses provided according to the present invention may feature a thermal conductivity at 90° C. between 0.8 and 1.2 $W*m^{-1}*K^{-1}$, or between 0.9 and 1.1 $W*m^{-1}*K^{-1}$ making it most suitable for use as lamp cover.

Figure 4:
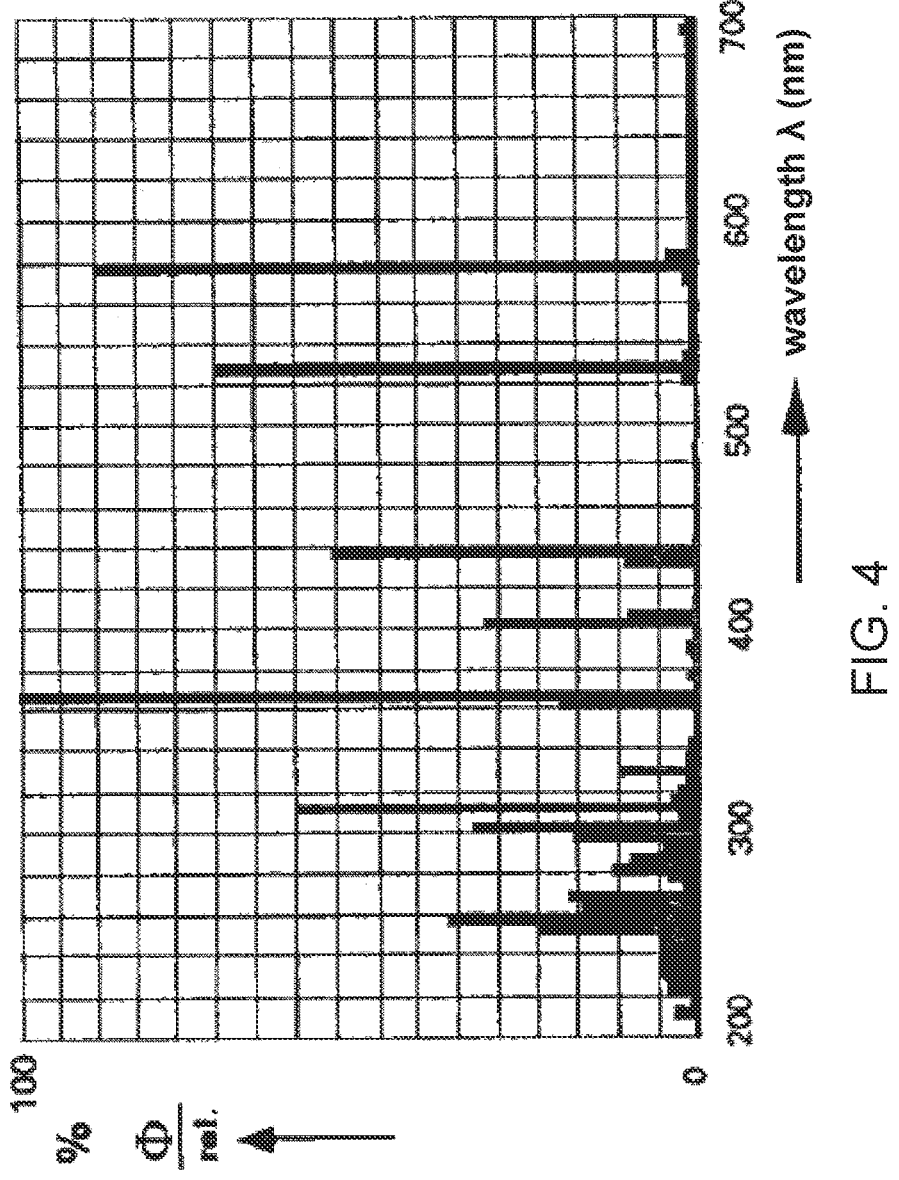
FIG. 4 illustrates the emission spectrum of an HOK 4 lamp.

The UVC-glasses and the UVC-glass covers made thereof have the following additional features:

The glasses provided according to the present invention are characterized by a particularly high solarization resistance. The solarization resistance can be determined by irradiating the glass with a HOK 4 lamp for 144 hours and comparing the transmittance at a wavelength of 220 nm before and after irradiation. The term "HOK 4 lamp" refers to the high pressure mercury-vapor lamp HOK 4/120 of Phillips. The emission spectrum of the HOK 4 lamp is shown in FIG. 4. The main emission of the lamp is at a wavelength of 365 nm. The power density at 200-280 nm in a distance of 1 m is 850 $\mu W/cm^2$. For the irradiation for 144 hours of the present invention, the distance between the HOK 4 lamp and the sample is chosen to be 7 cm.

The lower the difference between the transmittance before and after irradiation is, the higher is the solarization resistance. A high solarization resistance is associated with low solarization and vice versa. A high solarization correlates with a high induced extinction $Ext_{ind}$.

The induced extinction $Ext_{ind}$ can be determined based on the transmittance before and after irradiation with the HOK 4 lamp for 144 hours and the thickness of the glass sample using the following formula:

$$Ext_{ind} = -\frac{\ln\frac{T_{after}}{T_{before}}}{d}$$

$Ext_{ind}$ is the induced extinction, $T_{after}$ is the transmittance after irradiation with the HOK 4 lamp for 144 hours, $T_{before}$ is the transmittance before irradiation with the HOK 4 lamp for 144 hours, d is the sample thickness, and ln is the natural logarithm. If not indicated otherwise, the sample thickness d is given in cm so that the induced extinction is given in 1/cm. If not indicated otherwise, the transmittance before and after irradiation with the HOK 4 lamp are given for a wavelength of 220 nm. Thus, the induced extinction as described in the present disclosure refers to the induced extinction at a wavelength of 220 nm if not indicated otherwise.

In some embodiments, the induced extinction at a wavelength of 220 nm is at most 1.0/cm, at most 0.5/cm, at most 0.2/cm, at most 0.1/cm, at most 0.05/cm, at most 0.02/cm, or at most 0.01/cm. The induced extinction at a wavelength of 220 nm may for example be at least 0.001/cm, at least 0.002/cm, or at least 0.005/cm. The induced extinction at a wavelength of 220 nm may for example be from 0.001/cm to 1.0/cm, from 0.001/cm to 0.5/cm, from 0.002/cm to 0.2/cm, from 0.002/cm to 0.1/cm, from 0.002/cm to 0.05/cm, from 0.005/cm to 0.02/cm, from 0.005/cm to 0.01/cm.

The transmittance (at a reference thickness of 0.71 mm) at a wavelength of 220 nm after irradiation with the HOK 4 lamp for 144 hours may for example be at least 30%, at least 35%, at least 40% or at least 60%.

The transmittance (at a reference thickness of 0.71 mm) at a wavelength of 220 nm after irradiation with the HOK 4 lamp for 144 hours may for example be at most 95.0%, at most 90.0%, at most 85.0%, or at most 80.0%. The transmittance at a wavelength of 220 nm may for example be in a range of from 30.0% to 95.0%, from 35.0% to 90.0%, from 40.0% to 85.0%, or from 60.0% to 80.0%.

Due to the glass properties, the UVC-glass covers can be sealed hermetically, for example by the use of laser glass frit sealing. This hermetical sealing is important, since a number of UVGI-applications take place in either aqueous environments (e.g. biofilm treatment or water treatment), humid environments (e.g. sewage systems) and/or environments with elevated gas-pressure or under vacuum. Furthermore, the hermetical sealing allows the final device, e.g. a UVC-LED-lamp, to be autoclaved, so that it can be used in hospitals, in surgery, in laboratories or in any other environment where high hygienic standards are needed.

This is contrary to conventional glasses, quartz and/or fused silica glasses, which do not possess the thermic properties needed for laser frit sealing, and, thus, cannot be sealed hermetically. However, the glasses described herein are suitable to achieve crack free and tight glass frit connections.

The glasses provided according to the present invention may have a product CTE $[° C.^{-1}] \times T_4 [° C.]$ of at most 0.01, for example at most 0.0099 or at most 0.0098. The product may be at least 0.0075 or at least 0.0085. It has been shown that these glasses can show advantageous properties with regard to fusion stress and melting behavior.

"$T_4$" is the temperature at which the glass has a viscosity of $10^4$ dPa*s. $T_4$ can be measured by the methods known to the person skilled in the art for determining the viscosity of glass, e.g. according to DIN ISO 7884-1: 1998-02. "$T_{13}$" is the temperature at which the glass has a viscosity of $10^{13}$ dPa*s.

The average linear coefficient $\alpha$ of the thermal expansion (CTE) (at 20° C.; 300° C., according to ISO 7991) is in some embodiments between 7.0 and $12.0 \times 10^{-6}$ $K^{-1}$. The thermal expansion coefficient (CTE) may be less than $11.5 \times 10^{-6}$ $K^{-1}$. It may range from 7.5 to $<11 \times 10^{-6}$ $K^{-1}$, for example from 8.75 to $10.75 \times 10^{-6}$ $K^{-1}$, from 9.0 to $10.0 \times 10^{-6}$ $K^{-1}$, or from 9.2 to $9.8 \times 10^{-6}$ $K^4$. This allows adapting the thermal expansion properties to the overall thermal expansion properties of the UV-device and therefore prevents tensions within the glass cover. In some embodiments, the same or similar CTE is chosen for both the UVC-glass cover as well as the underlying UV-device (e.g. UVC-LED-package).

Another important property of the glasses is their excellent spatial homogeneity of the refractive index $n_d$ of the material. Optionally, a refractive index variation within the glass may correspond to a deformation of the wavefront passing through the glass, according to the following formula:

$$\Delta s = \Delta(n_d * d) = \Delta n_d * d + \Delta d * n_d$$

wherein As is the wavefront deviation, d is the thickness of the glass, $\Delta d$ is the thickness variation (difference between maximum and minimum thickness) and $\Delta n_d$ is the refractive index variation (difference between maximum and minimum refractive index) in the glass. The invention further provides glass articles having the indicated wavefront deviation.

The wavefront deviation can be calculated according to the formula above. The refractive index $n_d$ ($\lambda = 587.6$ nm) and the thickness may be determined at 20° C. In some embodiments the wavefront deviation is determined over and/or applies to a surface area of 1 $cm^2$. The wavefront deviation may be determined for a thickness of 10 mm of glass, or less; or 1 mm of glass or less. Optionally, the thickness may be at least 200 μm. The wavefront deviation may be less than ±0.1 mm, less than ±0.08 mm, in some embodiments less than ±0.035 mm, less than ±25 μm, less than ±15 μm, or less than ±5 μm. Optionally, the wavefront deviation may be between 0.1 μm and 250 μm, or between 1 μm and 100 μm, or between 2 μm and 85 μm.

The wavefront deviation may be measured axially, e.g. in the case of glass tubes, as used for example in discharge lamps; or laterally, e.g. in the case of rod sections, as used for lenses in UVC-LEDs.

The wavefront may also be measured by a wavefront sensor. This is a device which measures the wavefront aberration in a coherent signal to describe the optical quality or lack thereof in an optical system. Without being bound to a specific method, a very common method is to use a Shack-Hartmann lenslet array.

Alternative wavefront sensing techniques to the Shack-Hartmann system are mathematical techniques like phase imaging or curvature sensing. These algorithms compute wavefront images from conventional brightfield images at different focal planes without the need for specialized wavefront optics.

The glasses and glass articles provided according to the present invention may have a low content of wavefront deformations in the glass (striae, bubbles, streaks, etc.). In general, it can be distinguished between the global or long-range homogeneity of refractive index in the material and short-range deviations from glass homogeneity. Striae are spatially short-range variations of the homogeneity in a glass. Short-range variations are variations over a distance of about 0.1 mm and up to 2 mm, whereas the spatially long range global homogeneity of refractive index covers the complete glass piece.

In some embodiments an ultraviolet ray transmission filter may be used, which filters out certain non-desired UV-wavelengths, e.g. wavelengths above 220 nm.

The glasses for UV-covers provided according to the present invention may allow the shaping of lenses in order to optically shape the UV-beam, for example for directional focusing of the UV-light to the target.

Any beam angle between 10° and 180° is possible. In some embodiments 10° to 20°, 20° to 30°, 30° to 40°, 40° to 50°, 50° to 60°, 60° to 70°, 70° to 80°, 80 to 90° may be used. In some embodiments 15° to 35°, 25° to 45°, 35° to 60°, 45° to 90°, 75° to 120°, 90° to 145°, 120° to 180° may be used.

In some embodiments rather broad beam shapes, such as 90°, 120° or even 180°, are useful, for example in cases in which a surface of a certain size or a certain volume or a tube of a certain diameter needs to be decontaminated in one treatment.

In some embodiments narrow beam shapes such as 10°, 5° or even 1°, are useful. For example, narrow beam shapes can be used to concentrate the UV-exposure at the target site and avoid non-directional and undesired radiation, which would result in a less efficient energy-to-radiation ratio or exposure of UV-sensitive surfaces to UV-light. One example may be the limited decontamination of defined areas of an eye.

Furthermore, different lens shapes and beam angles may be used to solve complex pathogen-eradication tasks. For example, in cases in which UV-sensitive surfaces of different sensitivity levels are next to each other and need to be UV-exposed in one treatment. For example, it may be suitable to treat the skin of a patient in some areas with higher UV-exposure than in neighboring areas, e.g. during wound treatment and/or surgery, where the wound itself is exposed to less UV than the surrounding skin.

The invention provides also methods for the production of LED-packages with covers made with the inventive 220 nm-UVC-transparent glasses.

An LED package provided according to the present invention may comprise an LED chip, optionally: a substrate whereon the LED chip is mounted—e.g. made of PCB, polymer, inorganic material for example ceramic or metal;

optionally: a base plate in case including feedthroughs for electrical conductors for contacting the LED chip (metals, ceramics, glass ceramics, polymers);

a frame containing the LED chip being attached to or surrounding the base plate and building some kind of a cavity (metals, ceramics, glass ceramics, polymers);

a distal portion of the housing (cover) facing away and in distance from the chip being at least partially transparent closing the package or being made in total of a transparent material; wherein at least the transparent part of the cover is made of the UVC-transparent glass described herein.

Such windows may be flat or have a shape for changing the path of the light (i.e. lens-shape).

As mentioned previously, UVC-LEDs may be packaged and sealed in a way (e.g. laser frit sealing) so that they are autoclavable, sterilizable and resistant against fluids. Such UVC-LEDs may be used for sterilization of air and water, surfaces; and for medical/dental applications.

The UVC-LEDs having the UVC-transparent glass described herein possess further advantages in comparison to conventional UVGI-lamps or devices (such as mercury-vapor lamps), for example:

Instant on/off-function which allows an "on-demand disinfection" without wasted energy;

Directional emission (especially by the use of lenses which allow the control of the beam angle), which allows "targeted disinfection" with simple design;

Semiconductor durability, which allows the use in rugged, portable devices;

Low DC-power requirement, which increases the energy-efficacy and results in simple, inexpensive electrical drivers;

Compact packaging, which maximizes design flexibility;

Eco-friendly construction, since it allows easy disposal without harmful mercury exposure;

High optical performance;

High radiation power at defined wavelength;

Comparably low production price;

Small size

Traditionally, both low and medium pressure mercury lamps have been utilized in disinfection systems. However, there is a need to replace these light sources with high powered and energy-efficient UV-lights, such as for example UVC-LEDs. The UV-lamps and the UV-devices provided according to the present invention are more energy efficient as compared to conventional UVGI-lamps or -devices. This is because the glass may transmit more than 60% of the UV-light at 220 nm and therefore the ratio between energy-input and radiation-output is significantly improved.

This becomes important when these glasses are used as covers of UVC-LED-lamps. If the energy requirement of a conventional mercury-vapor-UV-lamp is set at 100%, the energy necessary to generate the same UV-radiation with the UVC-LEDs described herein is about 10 to 30%. In other words, if a conventional UV-lamp uses 10 W of energy to emit a certain UV-intensity the devices herein may use only between 1 and 3 W.

As mentioned previously, another advantage of the UVC-transparent glasses described herein are their high thermal conductivity (4), which may be between 0.75 and 1.25 $W*m^{-1}*K^{-1}$ at 90° C., in some embodiments about 1.0 $W*m^{-1}*K^{-1}$. This superior thermal conductivity increases the lifetime of the device, since excess heat can dissipate easily before harming other parts of the device. This is, for example, in contrast to quartz-glasses, which normally have a less optimal thermal conductivity.

Thus, in some embodiments, the method provided according to present invention may include UV-lamps with an energy efficiency index (EEI) of <0.11 according to the REGULATION (EU) No 874/2012 in case of non-directional UV-lamps and an energy efficiency index (EEI) of ≤0.13 according to the REGULATION (EU) No 874/2012 in case of directional UV-lamps.

The methods described herein may be used for eradication of pathogens from any kind of surface, including UV-sensitive surfaces, UV-sensitive liquid and/or UV-sensitive gas.

Of course the methods described herein may be used also for eradication of a variety UV-sensitive pathogenic organisms, such as viruses (such as for example influenza- or coronaviridae, such as SARS-CoV-2, especially resistant virus mutations, such as for example SARS-CoV2-D614G), bacteria (including spores), pathological yeasts, mold, and the like.

Potential applications can be selected from the list of uses comprising hand sanitizers (e.g. on private and public toilets), room sanitizers in health care environments, pathogen-eradication in preparation to or during or after surgery, wound treatment, eye treatment, food disinfection (e.g. during food production and/or meat, dairy or vegetable counter in supermarkets), livestock disinfection (especially in cases of intensive animal husbandry, such as for example laying batteries), production of pharmaceutical compounds and/or food production processes, storage facilities and/or disinfection of UV-sensitive surfaces which are often in contact with many different users, for example keyboards, handles, handrails, tooth brushes, hair brushes, ornaments, touch-devices, shaving razors, or kids toys.

The UVC-devices disclosed herein can also be used for a wide range of applications as "analytical instrumentation", for example:

HPLC (high-performance liquid chromatography): Used in analysis for detecting chemicals and compounds in life sciences;

Spectrometers: Used in multiple applications in tests and analysis across biotech, life sciences and environmental monitoring; and Water quality monitoring sensors: Used for detecting chemicals in water (e.g. in the course of fracking, in cases of general water security or before the disposal of treated wastewater).

In some embodiments the UVC-devices disclosed herein may comprise devices for "water disinfection". In that respect UVC LEDs are advantageous as compared to traditional mercury lamps, which require a long warm up time (anywhere from 50 seconds to 10 minutes) to reach the required germicidal intensity. In addition, frequent on/off cycles can diminish lifetime by 50 percent or more.

Consequently, mercury lamps in these applications need to be kept on all day, increasing the frequency of lamp replacement, ozone generation and rising power consumption. By contrast, the instant on-off capability of UVC LEDs enables on-demand disinfection, which reduces power consumption significantly. Additionally, the frequent on/off-cycles do not diminish LED lifetime, helping lower operating and maintenance costs.

Further uses of the UVC-devices disclosed herein, especially in cases of UV-sensitive surfaces, liquids or gases, may comprise:

Protein analysis, i.e. the bioinformatics study of protein structure and function using database searches, sequence comparisons, structural and functional predictions.

Molecular identification, i.e. a process of comparing specific pieces of DNA between organisms.

Cytometry, i.e. in biotechnology, flow cytometry is a laser- or impedance-based, biophysical technology employed in cell counting, cell sorting, biomarker detection and protein engineering, by suspending cells in a stream of fluid and passing them through an electronic detection apparatus.

Biofilm treatment systems, i.e. systems which employ the use of bacteria, fungi, algae, and protozoa to remove organic and inorganic materials from the surrounding liquid.

Nitrate and/or NOx-measurement, which is normally done at wavelengths of about 230 nm.

Skin treatment in order to improve dermatologic conditions (e.g. psoriasis, vitiligo, itching, neurodermatitis, acne, actinic dermatitis, phototherapy, pityriasis rosea, etc.).

Thus, in some embodiments the use of the UV-LED-module may be selected from the group of water disinfection, analytical instrumentation (HPLC, spectrometers, water monitoring sensors), air purification, air disinfection, surface disinfection (e.g. keyboard disinfection, escalator handrail UV sterilizer), cytometry, molecular identification, protein analysis, biofilm treatment, curing, lithography, vegetable growth, skin cure, germ detection, drug discovery, protein analysis, induction of skin vitamine-D3-production and/or sterilization.

Thus, in some embodiments the invention pertains to uses of the glass as a hermetically sealing lens cap for an UV-LED-module, e.g. for applications selected from the group of water disinfection, analytical instrumentation (HPLC, spectrometers, water monitoring sensors), air purification, air disinfection, surface disinfection (e.g. keyboard disinfection, escalator handrail UV sterilizer), cytometry, molecular identification, protein analysis, biofilm treatment, curing, lithography, vegetable growth, skin cure (psoriasis, vitiligo, itching, neurodermatitis, acne, actinic dermatitis, phototherapy, pityriasis rosea), germ detection, drug discovery, protein analysis, induction of skin vitamine-D3-production and/or sterilization.

The glass may be a soda lime glass. In some embodiments, glass comprises the following components (in mol % based on oxides):

| Component | Content [mol %] |
|---|---|
| $SiO_2$ | 40 to 85 |
| $Al_2O_3$ | 0 to 25 |
| $Na_2O$ | 0 to 18 |
| $K_2O$ | 0 to 15 |
| MgO | 0 to 10 |
| $B_2O_3$ | 0.1 to 4 |
| $Li_2O$ | 0 to 10 |
| ZnO | 0 to 5 |
| CaO | 0 to 16 |
| BaO | 0 to 12 |
| $ZrO_2$ | 0 to 5 |
| $SnO_2$ | 0 to 3 |
| SrO | 0 to 4 |
| $F^-$ | 0 to 6 |
| $Cl^-$ | 0 to 1 |

In some embodiments, the glass comprises the following components (in mol % based on oxides):

| Component | Content [mol %] |
|---|---|
| $SiO_2$ | 60 to 84 |
| $Al_2O_3$ | 0 to 10 |
| $B_2O_3$ | 0.5 to 3.5 |
| $Li_2O$ | 0 to 3 |

16

-continued

| Component | Content [mol %] |
|---|---|
| $Na_2O$ | 0 to 15 |
| $K_2O$ | 0 to 12 |
| MgO | 0 to 6 |
| CaO | 0 to 6 |
| SrO | 0 to 4 |
| BaO | 0 to 8 |
| $F^-$ | 0 to 6 |
| $Cl^-$ | 0 to 0.8 |
| $R_2O$ | 5 to 25 |
| RO | 0 to 6 |

Wherein "$R_2O$" refers to the alkali metal oxides $Li_2O$, $Na_2O$ and $K_2O$; and "RO" denotes the alkaline earth metal oxides MgO, CaO, BaO and SrO.

The glasses may contain $SiO_2$ in a proportion of at least 40 mol %, or at least 60 mol %. $SiO_2$ contributes to the hydrolytic resistance and transparency of the glass. If the $SiO_2$ content is too high, the melting point of the glass is too high. The temperatures $T_4$ and $T_g$ also rise sharply. Therefore, the content of $SiO_2$ should be limited to a maximum of 78 mol %, or to a maximum of 80 mol %, or to maximum of 81 mol %, or to a maximum of 82 mol %, or to a maximum of 85%.

In some embodiments, the content of $SiO_2$ is at least 61 mol %, at least 63 mol % or at least 65 mol %, at least 68 mol %, at least 69 mol %, or at least 70 mol %, or at least 72 mol %, or at least 75 mol %. The content can be limited to a maximum of 84 mol % or a maximum of 82 mol %, or a maximum of 81 mol %, or a maximum of 80 mol %.

The glasses may contain $Al_2O_3$ in a maximum proportion of 10 mol %. $Al_2O_3$ contributes to the phase separation stability of the glasses, but in larger proportions reduces the acid resistance. Furthermore, $Al_2O_3$ increases the melting temperature and $T_4$. Thus, the content of this component should be limited to a maximum of 25 mol %, or to a maximum of 9 mol %, or to a maximum of 8 mol %, or to a maximum of 7 mol %, or to a maximum of 5 mol %, or to a maximum of 4.5 mol %. In some embodiments $Al_2O_3$ is used in a small proportion of at least 0.1 mol %, at least 0.2 mol %, or at least 0.5 mol %, or at least 1.0 mol %. In some embodiments the glass may be free of $Al_2O_3$.

The glasses may contain $B_2O_3$ in a proportion of at least 0.5 mol %. $B_2O_3$ has an effect on the melting properties of glass. $B_2O_3$ may be limited to up to 4.0 mol %, up to 3.5 mol %, up to 3.0 mol %, up to 2.5 mol %, or up to 2.0 mol %. Limiting the amount of $B_2O_3$ may be advantageous for reducing transmittance at 200 nm. The content of $B_2O_3$ can be at least 1.0 mol %, at least 1.2 mol %, or at least 1.5 mol %.

Optionally, the ratio of the sum of the contents (in mol %) of $B_2O_3$, $R_2O$ and RO to the sum of the contents (in mol %) of $SiO_2$ and $Al_2O_3$ is at most 0.4, at most 0.35, or at most 0.3. In some embodiments, this value is at least 0.1, at least 0.15, or at least 0.2.

The glasses may contain $Li_2O$ in a proportion of up to 10.0 mol %, or up to 3.0 mol %, or up to 2.8 mol %, or up to 2.5 mol %. Optionally, the glass contains only a small amount of $Li_2O$, e.g. to a maximum of 3.0 mol %, to a maximum of 2.8 mol %, to a maximum of 2.5 mol %, to a maximum of 2.0 mol %, or to a maximum of 1.9 mol %, or the glass is free of $Li_2O$. In some embodiments the content of $Li_2O$ is between 1 mol % and 2 mol %.

The glasses may contain $Na_2O$ in a proportion of up to 18 mol %, up to 15 mol %, up to 12 mol %, up to 11 mol %, or up to 10 mol %. $Na_2O$ increases the fusibility of the glasses. Sodium oxide also leads to a reduction in UV transmission and an increase in the coefficient of thermal expansion (CTE). The glass may contain $Na_2O$ in a proportion of at least 1 mol %, at least 2 mol %, at least 4 mol %, at least 5 mol %, or at least 6 mol %. In some embodiments the content of $Na_2O$ is a maximum of 5 mol %, or a maximum of 4 mol %. In some embodiments the glass may be free of $Na_2O$.

The glasses may contain $K_2O$ in a maximum proportion of 15 mol %. Its content may be at least 1 mol %, at least 2 mol %, at least 4 mol %, at least 5 mol %, or at least 6 mol %. The content of this component may be limited to a maximum of 15 mol %, to a maximum of 12 mol %, to a maximum of 10 mol %, to a maximum of 9 mol %, or a maximum of 8 mol %. In some embodiments the glass may be free of $K_2O$.

In some embodiments, the ratio of the contents of $Na_2O$ to $K_2O$ in mol % may be at least 1.0, for example at least 1.1. In some embodiments the said ratio is at most 2, for example at most 1.5. Both oxides serve to improve the fusibility of the glass. In some embodiments the ratio is between 1.1 and 1.3.

The amount of $R_2O$ in the glasses may be limited to not more than 25 mol %, not more than 22 mol %, or not more than 20 mol %. The glasses may contain $R_2O$ in amounts of at least 5 mol %, at least 8 mol %, or at least 10 mol %. In some embodiments the content of $R_2O$ is between 10 mol % and 20 mol %. $R_2O$ may contribute to reducing transmittance at 200 nm.

The glasses may contain MgO in a proportion of up to 10 mol %, up to 6 mol %, up to 4 mol %, or up to 2 mol %. MgO may be advantageous for fusibility, but in high proportions it proves to be problematic with regard to the desired UV transmission and the tendency to phase separation. Some embodiments are free of MgO.

The glasses may contain CaO in a proportion of up to 16 mol %, up to 6 mol %, up to 4 mol %, or up to 2 mol %, or up to 1 mol %. CaO may be advantageous for fusibility, but in high proportions it proves to be problematic with regard to the desired UV transmission. Some embodiments are free of CaO or contain only little CaO, e.g. at least 0.1 mol %, at least 0.3 mol %, or at least 0.5 mol %.

The glasses may contain SrO in a proportion of up to 4 mol %, up to 1 mol %, or up to 0.5 mol %. SrO may be advantageous for fusibility, but in high proportions it proves to be problematic with regard to the desired UV transmission. Some embodiments are free from SrO.

The glasses may contain BaO in a proportion of up to 12 mol %, or up to 8 mol %, or up to 6 mol %, or up to 5 mol %, or up to 4 mol %. BaO leads to an improvement of the hydrolytic resistance. However, a too high barium oxide content leads to phase separation and, thus, to instability of the glass. Some embodiments contain BaO in amounts of at least 0.5 mol %, at least 1.0 mol %, or at least 1.5 mol %. In some embodiments the content of BaO is between 1.0 mol % and 4.0 mol %. In some embodiments the glass may be free of BaO.

It has been shown that the alkaline earth oxides RO have a great influence on the phase separation tendency. In a design form, special attention is therefore paid to the contents of these components and their relationship to one another. Thus, the ratio of BaO in mol % to the sum of the contents of MgO, SrO and CaO in mol % may be at least 2. Optionally, this value is at least 5, or at least 10, or at least 20. In some embodiments, the value may be at least 40, or even at least 50. BaO may offer the most advantages in terms of phase separation and hydrolytic resistance compared to the other alkaline earth metal oxides. However, the ratio should not exceed 120 or 100. In some embodiments, the glass contains at least small amounts of CaO and BaO and is free of MgO and SrO. In some embodiments, the ratio is between 50 and 100.

Advantageous properties may be obtained if the ratio of the proportion of CaO in the glass to BaO in mol % is less than 0.2. For example, this ratio may be less than 0.15 or less than 0.1. In some embodiments the ratios are even lower, for example less than 0.08, or less than 0.06, and in some embodiments this ratio is at least 0.03. In some embodiments the ratio is between 0 and 0.1.

In some embodiments, the glass has a mol % ratio of $B_2O_3$ to BaO of at least 0.1 and at most 2.0. In some embodiments, the ratio is at least 0.2, or at least 0.5 and, in some embodiments, the said ratio is limited to a maximum of 1.8, or of 1.5, or of 1.2. In some embodiments, the ratio may be limited to a maximum of 1.0 or 0.8. In some embodiments, the ratio is not less than 0.2 and not more than 2.0, or in some embodiments not less than 0.5 and not more than 1.8; some embodiments the ratio is between 0.2 and 1.0.

The proportion of RO in the glasses provided according to the present invention can be at least 0.3 mol %. Alkaline earth metal oxides may be advantageous for fusibility, but in high proportions they prove to be problematic with regard to the desired UV transmission. In some embodiments, the glass contains a maximum of 5 mol % RO. In some embodiments the proportion of RO is between 1 and 5 mol %.

The sum of the contents in mol % of alkaline earth metal oxides and alkali metal oxides, $RO+R_2O$, can be limited to a maximum of 30 mol %. Some embodiments can contain these components in quantities of maximum 25 mol %. In some embodiments the content of these oxides is at least 5 mol %, at least 10 mol %, or at least 12 mol %. In some embodiments the $RO+R_2O$-proportion is between 12 and 20 mol %. These components increase the phase separation tendency and reduce the hydrolytic resistance of the glasses in too high proportions.

The ratio of the contents in mol % of $B_2O_3$ to the sum of the contents of $R_2O$ and RO in mol % may be at least 0.01, at least 0.02, or at least 0.05. The ratio can be limited to a maximum of 1.5, a maximum of 1.0, or a maximum of 0.5. In some embodiments the $B_2O_3/(RO+R_2O)$-proportion is between 0.05 and 0.2. Alkali or alkaline earth borates can form during glass phase separation, if too much alkali or alkaline earth oxide is present in relation to $B_2O_3$. It has been proven to be advantageous to adjust the above ratio.

To ensure that the melting properties, including $T_g$ and $T_4$, are within the desired range, it may be advantageous to set the ratio of the content of $B_2O_3$ to the sum of the contents of $SiO_2$ and $Al_2O_3$ in mol % within a narrow range. In some embodiments, this ratio is at least 0.015 and/or at most 0.04. In some embodiments the $B_2O_3/(SiO_2+Al_2O_3)$-ratio is between 0.017 and 0.03.

The ratio of the proportions in mol % of the sum of the alkali metal oxides $R_2O$ to the sum of the alkaline earth metal oxides RO may be >1, for example >2 or >4. In some embodiments, this ratio is at most 15, at most 10 or at most 7.5. In some embodiments the ratio is between 4 and 10.

The glasses may contain $F^-$ in a content of 0 to 6 mol %. In some embodiments the content of $F^-$ is at most 4 mol % or at most 2 mol %. In some embodiments, at least 0.5 mol %, or at least 1 mol % of this component is used. Component F⁻ improves the fusibility of the glass and influences the UV edge towards smaller wavelengths.

The glasses may contain Cl⁻ in a content of less than 1 mol %, for example less than 0.9 mol %, or less than 0.8 mol %. Suitable lower limits are 0.1 mol %, or 0.2 mol %.

The glasses may contain ZnO in a content of less than 5 mol %, for example less than 2.5 mol %, or less than 1 mol %. Suitable lower limits are 0.01 mol %, or 0.05 mol %. In some embodiments the glass may be free of ZnO.

The glasses may contain $ZrO_2$ in a content of less than 5 mol %, less than 2.5 mol %, or less than 1 mol %. Suitable lower limits are 0.01 mol %, or 0.05 mol %. In some embodiments the glass may be free of $ZrO_2$.

The glasses may contain $SnO_2$ in a content of less than 3 mol %, for example less than 2 mol %, or less than 1 mol %. Suitable lower limits are 0.01 mol %, or 0.05 mol %. In some embodiments the glass may be free of $SnO_2$.

When this description states that the glass is free of a component or does not contain a certain component, it means that this component may at most be present as an impurity. This means that it is not added in significant quantities. Non-significant quantities are quantities of less than 0.5 ppm, for example less than 0.25 ppm, less than 0.125 ppm or less than 0.05 ppm.

In some embodiments, the glass has less than 10 ppm $Fe_2O_3$, for example less than 5 ppm or less than 4 ppm. In some embodiments, the glass has less than 10 ppm $TiO_2$, for example less than 5 ppm or less than 4 ppm. In some embodiments, the glass has less than 3.5 ppm arsenic, for example less than 2.5 ppm or less than 1.0 ppm. In some embodiments, glass containing less than 3.5 ppm antimony, less than 2.5 ppm antimony, or less than 1.0 ppm antimony is provided. Besides the negative effects on UV-transmission and solarization, especially arsenic and antimony are toxic and dangerous to the environment and should be avoided.

Optionally, the glass includes the following components (in mol % on oxide basis):

| Component | Content [mol %] |
|---|---|
| $SiO_2$ | 68 to 82 |
| $Al_2O_3$ | 0.1 to 7 |
| $B_2O_3$ | 1.0 to 3.0 |
| $Li_2O$ | 0 to 3.0 |
| $Na_2O$ | 1 to 12 |
| $K_2O$ | 1 to 10 |
| CaO | 0 to 4 |
| SrO | 0 to 1 |
| BaO | 0.5 to 6 |
| F⁻ | 0 to 6 |

In some embodiments, the glass includes the following components in mol %:

| Component | Content [mol %] |
|---|---|
| $SiO_2$ | 69 to 81 |
| $Al_2O_3$ | 0.2 to 5 |
| $B_2O_3$ | 1.2 to 2.5 |
| $Li_2O$ | 0 to 2.5 |
| $Na_2O$ | 2 to 11 |
| $K_2O$ | 2 to 9 |
| CaO | 0 to 2 |
| SrO | 0 to 0.5 |
| BaO | 1.0 to 5 |
| F⁻ | 0.5 to 4 |

In some embodiments, the glass includes the following components in mol %:

| Component | Content [mol %] |
|---|---|
| $SiO_2$ | 70 to 80 |
| $Al_2O_3$ | 0.5 to 4.5 |
| $B_2O_3$ | 1.5 to 2.0 |
| $Li_2O$ | 0 to 2 |
| $Na_2O$ | 4 to 10 |
| $K_2O$ | 4 to 8 |
| CaO | 0 to 1 |
| SrO | 0 to 0.5 |
| BaO | 1.5 to 4 |
| F⁻ | 1 to 2 |

The invention also provides glass articles made from the glass described herein. The glass article can be produced by drawing processes known for glass tubes and rods. Depending on the desired shape, the person skilled in the art will choose a suitable manufacturing process, e.g. ingot casting for bars, floating or down draw for producing panes. In some embodiments, the cooling of the glass in the process is adjusted so that the desired properties are achieved.

In some embodiments, the glass article is produced using the Danner or the Vello method. In the Vello method, the glass melt flows vertically downwards (in the direction of the gravitational force) through a shaping tool made of an outlet ring and a needle. The shaping tool forms a negative form (matrix) of the generated cross-section of the glass tube or the glass rod. In the manufacture of glass tubes, a needle is arranged as a shaping part in the center of the shaping tool.

The difference between the Vello and the down draw method is first of all that the glass melt in the Vello method is deflected horizontally after it leaves the forming tool and, secondly, in the fact that the needle has a passage in the Vello method, through which blown air flows. As with the Danner method, the blown air ensures that the resulting glass tube does not collapse. In the down draw method, the solidified glass melt is separated without prior redirection. Since there is no redirection, one can also refrain from the use of blown air during the production of glass tubes.

In some embodiments, the invention relates to a glass article made of the glass disclosed herein. The thickness of the glass article, for example the wall thickness in the case of a glass tube, can be at least 0.1 mm or at least 0.3 mm. The thickness can be limited to up to 3 mm or up to 2 mm. The outside diameter of the glass article, e.g. the outside diameter of a glass tube or glass rod, can be up to 50 mm, up to 40 mm, or up to 30 mm. The outside diameter can for example be at least 1 mm, at least 2 mm, or at least 3 mm.

Thus, the present invention pertains also to the following embodiments:

In some embodiments the invention pertains to a method for eradicating pathogens, the method comprising exposing the pathogen to germicidal UV light with a wavelength of about 220 nm, wherein the UV light is irradiated by a UV lamp having a lamp cover made of a glass having a total platinum content of less than 3.5 ppm.

In some embodiments said pathogen exposed to germicidal UV light resides on a UV-sensitive material, which is sensitive to UV-radiation above 222 nm. In yet another aspect said UV-sensitive material is a biological tissue surface such as the eye or skin of an animal, wherein the animal is selected from an insect, invertebrate, vertebrate, mammal and/or human.

In some embodiments said eradication of pathogen after treatment is >99% according to BS ISO 22196:2011-08-31.

In some embodiments said UV-exposure of the pathogen is at least in the range from 2,000 to 8,000 microwatt seconds per square centimeter ($\mu W \cdot s/cm^2$).

In some embodiments all or part the cover of said UV lamp is shaped in form of a lens.

In some embodiments the invention pertains to a glass having a transmittance at a wavelength of 220 nm of at least 30%, wherein the glass has a total platinum content of not more than 3.5 ppm, in some embodiments not more than 3 ppm, not more than 2.5 ppm, not more than 2 ppm.

For many applications, a certain transmittance in the UV range is desirable. The glasses may have a ratio of the transmittance at 220 nm to the transmission at 200 nm of at least 20.00 or at least 30.00, for example at most 100.00 or at most 80.00.

In some embodiments said glass comprises one or more UV-blocking impurities selected from rhodium, lead, cadmium, mercury, hexavalent chromium, iron, titanium, and any combination thereof. In some embodiments said glass comprises a total platinum content below 1.0 ppm.

The wavefront deviation may be less than ±0.1 mm, less than ±0.08 mm, less than ±0.035 mm, less than ±25 μm, less than ±15 μm, or less than ±5 μm. Optionally, the wavefront deviation may be between 0.1 μm and 250 μm, or between 1 μm and 100 μm, or between 2 μm and 85 μm. In some embodiments said glass comprises the following components in the indicated amounts (in mol %):

| Component | Content [mol %] |
|---|---|
| $SiO_2$ | 40 to 85 |
| $Al_2O_3$ | 0 to 25 |
| $Na_2O$ | 0 to 18 |
| $K_2O$ | 0 to 15 |
| MgO | 0 to 10 |
| $B_2O_3$ | 0.1 to 4 |
| $Li_2O$ | 0 to 10 |
| ZnO | 0 to 5 |
| CaO | 0 to 16 |
| BaO | 0 to 12 |
| $ZrO_2$ | 0 to 5 |
| $SnO_2$ | 0 to 3 |
| SrO | 0 to 4 |
| $F^-$ | 0 to 6 |
| $Cl^-$ | 0 to 1 |

In some embodiments the invention pertains to the use of said glass as a hermetically sealing lens cap for a UV-LED-module, e.g. for applications selected from the group of water disinfection, analytical instrumentation (HPLC, spectrometers, water monitoring sensors), air purification, air disinfection, surface disinfection (e.g. keyboard disinfection, escalator handrail UV sterilizer), cytometry, molecular identification, protein analysis, biofilm treatment, curing, lithography, vegetable growth, skin cure (psoriasis, vitiligo, itching, neurodermatitis, acne, actinic dermatitis, phototherapy, pityriasis rosea), germ detection, drug discovery, protein analysis, induction of skin vit-D3-production and/or sterilization.

In some embodiments, the invention relates to a glass articles comprising or consisting of the glass described herein. In some embodiments, the glass article has at least one polished surface. Optionally, the glass article has at least one chamfered edge. The polished surface may have a surface roughness Ra of less than 10 nm or less than 5 nm. Chamfered edges are more impact resistant, in particular more resistant to chipping than non-chamfered edges.

Thermal and/or Chemical Tempering

Optionally, the manufacturing process comprises the step of chemical and/or thermal tempering of the glass article. The "tempering" is also referred to as "hardening" or "toughening".

In some embodiments, the glass article is toughened on at least one surface, in particular thermally and/or chemically toughened. For example, it is possible to chemically temper glass articles by ion exchange. In this process, small alkali ions in the article are usually replaced by larger alkali ions. Often, the smaller sodium is replaced by potassium. However, it is also possible that the very small lithium is replaced by sodium and/or potassium. Optionally, it is possible that alkali ions are replaced by silver ions. Another possibility is that alkaline earth ions are exchanged for each other according to the same principle as the alkali ions. In some embodiments, the ion exchange takes place in a bath of molten salt between the article surface and the salt bath. Pure molten salt, for example molten $KNO_3$, can be used for the exchange. However, salt mixtures or mixtures of salts with other components can also be used. The mechanical resistance of an article can further be increased if a selectively adjusted compressive stress profile is built up within the article. This can be achieved by mono- or multistage ion exchange processes.

By replacing small ions with large ions or by thermal tempering, a compressive stress is created in the corresponding zone, which drops from the surface of the glass article towards the center. The maximum compressive stress is just below the glass surface and is also referred to as CS (compressive stress). CS is a stress and is expressed in units of MPa. The depth of the compressive stress layer is abbreviated as "DoL" and is given in the unit μm. CS and DoL may be measured using the FSM-60LE apparatus from Orihara.

In some embodiments, CS is greater than 100 MPa. In some embodiments, CS is at least 200 MPa, at least 250 MPa, or at least 300 MPa. In some embodiments, CS is at most 1,000 MPa, at most 800 MPa, at most 600 MPa, or at most 500 MPa. In some embodiments, CS is in a range from >100 MPa to 1,000 MPa, from 200 MPa to 800 MPa, from 250 MPa to 600 MPa, or from 300 MPa to 500 MPa.

In some embodiments, the glass article is thermally toughened. Thermal toughening is typically achieved by rapid cooling of the hot glass surface. Thermal toughening has the advantage that the compressive stress layer can be formed deeper (larger DoL) than with chemical toughening. This makes the glasses less susceptible to scratching, since the compressive stress layer cannot be penetrated as easily with a scratch as with a thinner compressive stress layer.

The glasses or glass articles can, for example, be subjected to a thermal tempering process after a melting, shaping, annealing/cooling process and cold post-processing steps. In this process, glass bodies (e.g. a previously described glass article or a preliminary product), for example flat glass, may be fed horizontally or suspended into a device and rapidly heated to a temperature up to a maximum of 150° C. above the transformation temperature TG. The surfaces of the glass body are then rapidly cooled, for example by blowing cold air through a nozzle system. As a result of the rapid cooling of the glass surfaces, they are frozen in an expanded network, while the interior of the glass body cools slowly and has time to contract more. This creates a compressive stress in the surface layer and a tensile stress in the interior. The amount of compressive stress depends on various glass parameters such as $CTE_{glass}$ (average linear coefficient of thermal expansion below Tg), $CTE_{liquid}$ (average linear coefficient of thermal expansion above Tg), strain point, softening point, Young's modulus and also on the amount of heat transfer between the cooling medium and the glass surface as well as the thickness of the glass bodies.

In some embodiments, a compressive stress of at least 50 MPa is generated. As a result, the flexural strength of the glass bodies can be doubled to tripled compared to non-toughened glass. In some embodiments, the glass is heated to a temperature of 750 to 800° C. and tempered fast in as stream of cold air. Optionally, the blowing pressure may be from 1 to 16 kPa. With the glasses or glass articles described herein, values of compressive stress of 50 to 250 MPa, in particular 75 to 200 MPa, for example, are achieved on commercially available systems.

In some embodiments, the glass article has a compressive stress layer with a compressive stress of at least 50 MPa, such as at least 75 MPa, at least 85 MPa or at least 100 MPa. The glass article may have a compressive stress layer on one, two or all of its surfaces. The compressive stress of the compressive stress layer may be limited to at most 250 MPa, at most 200 MPa, at most 160 MPa or at most 140 MPa. These compressive stress values may be present, in particular, in thermally toughened glass articles.

In some embodiments, the depth of the compressive stress layer of the glass article is at least 10 μm, at least 20 μm, at least 30 μm, or at least 50 μm. In some embodiments, this layer may even be at least 80 μm, at least 100 μm, or at least 150 μm. Optionally, the DoL is limited to at most 2,000 μm, at most 1,500 μm, at most 1,250 μm, or at most 1,000 μm. In particular, the DoL can be from 10 μm to 2,000 μm, from 20 μm to 1,500 μm, or from 30 μm to 1,250 μm. In some embodiments, the glass article is thermally toughened with a DoL of at least 300 μm, at least 400 μm or at least 500 μm. Optionally, the DoL may be at most 2,000 μm, at most 1,500 μm, or at most 1,250 μm. In some embodiments, the DoL is from 300 μm to 2,000 μm, from 400 μm to 1,500 μm, or from 500 μm to 1,250 μm.

Examples

Figure 3:
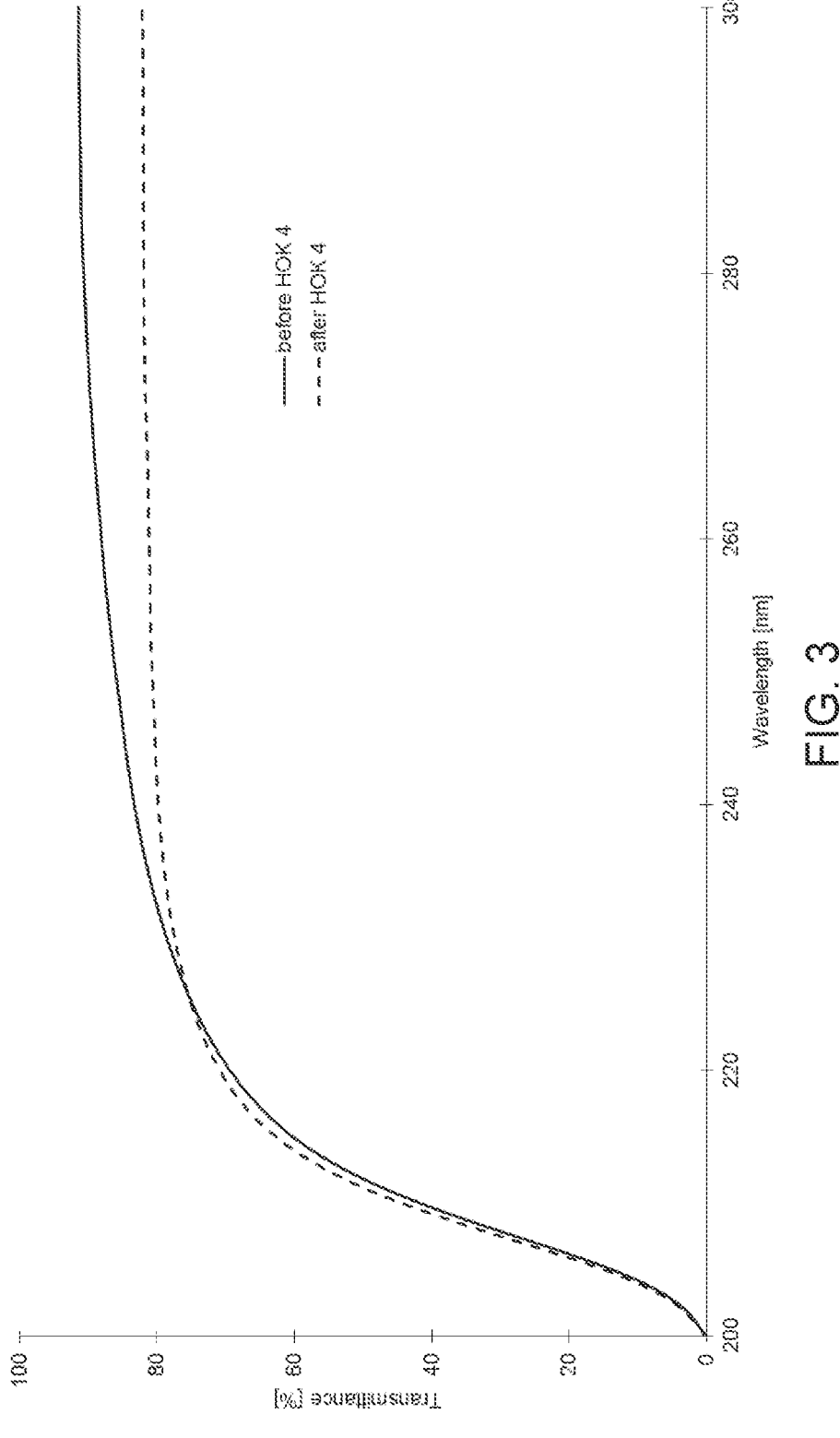
FIG. 3 illustrates transmittance spectra for some of the glasses provided according to the present invention.

Alkali-containing silicate glasses provided in accordance with the glass composition as described in the present disclosure were obtained under reducing melting conditions. Samples having a thickness of 0.71 mm have been tested for transmittance in the wavelength range of from 200 nm to 300 nm before and after irradiation with the HOK 4 lamp. The results are shown in FIG. 3.

In particular, regarding the particularly relevant wavelengths of $\lambda$=200 nm and $\lambda$=220 nm, the results obtained are summarized in the following table.

| | Transmittance before HOK 4 irradiation [%] | Transmittance after HOK 4 irradiation [%] |
|---|---|---|
| $\lambda$ = 200 nm | 0.2 | 0.2 |
| $\lambda$ = 220 nm | 69.4 | 70.8 |

The glass has a low transmittance at 200 nm and a high transmittance at 220 nm. The transmittance at both 200 nm and 220 nm remains substantially unchanged after irradiation with the HOK 4 lamp for 144 hours.

Referring now to the drawings, FIGS. 1A-1F illustrate potential uses of the UV-transparent glasses in different LED-packages. The form of the glass lens 1 allows the focusing or dispersion of the UV-light, depending on the specific application. Furthermore, the cover glass 1 may surround the UV-source (e.g. an UV-LED) 4 so that UV-light is emitted also laterally (cf. FIGS. 2C to 2F). Reflective elements at the back of the casing 3 may improve the light emitting efficacy. As casing 3 an aluminium nitride ceramic—(AIN ceramic) with high thermal conductivity may be used. The LED 4 and the glass cover 1 may be metal soldered 2 to the casing 3.

In FIGS. 2A-2E, instead of metal soldering 2 the glass to the casing 3 (see FIG. 2A), the UV-transparent glasses 1 provided according the present invention may also be attached to the casing via laser frit sealing 6 (see FIG. 2B to 2E). The LED 4, which may be metal soldered 2 to the casing 3, may be additionally fully encapsulated in transparent encapsulation material 5. Such encapsulation material may be copolymers of methyl methacrylate and acyloximino methacrylate ester. In the examples poly-(methyl methacrylate-co-3-methacryloyl-oximino-2-butanone) was used. Due to the laser frit sealing 6, the LED-elements are then fully protected against environmental influences and, thus, this setup is most suitable for harsh environmental conditions, especially when strong acidic cleaners and/or disinfectants are used regularly. Again, as casing 3 an aluminium nitride ceramic—(AIN ceramic) with high thermal conductivity may be used. Again, reflective elements at the back of the casing 3 may improve the light emitting efficacy.

FIG. 3 shows transmittance spectra for some of the glasses provided according to the present invention.

FIG. 4 shows the emission spectrum of an HOK 4 lamp.

While this invention has been described with respect to at least one embodiment, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. A glass having a transmittance at a wavelength of 220 nm of at least 30% and a transmittance at a wavelength of 200 nm of less than 4.0%, the glass having a total platinum content of less than 3.5 ppm, wherein the glass comprises the following components in the indicated amounts (in mol %):

| Component | Content [mol %] |
|---|---|
| $SiO_2$ | 70 to 80 |
| $Al_2O_3$ | 0.5 to 4.5 |
| $B_2O_3$ | 1.5 to 2.0 |
| $Li_2O$ | 0 to 2 |
| $Na_2O$ | 4 to 10 |
| $K_2O$ | 4 to 8 |
| CaO | 0 to 1 |
| SrO | 0 to 0.5 |
| BaO | 1.5 to 4 |
| $F^-$ | 0 to 2. |

2. The glass of claim 1, wherein the glass has a transmittance of at least 75% at wavelengths of at least one of 260 nm, 280 nm or 310 nm.

3. The glass of claim 1, wherein the glass has a transmittance of at least 40% at a wavelength of 220 nm.

4. The glass of claim 1, wherein the glass comprises a total content of $Fe_2O_3$ from 0.5 ppm to 10 ppm.

5. The glass of claim 4, wherein the glass has a content of $Fe_2O_3$ from 1 ppm to 10 ppm, a content of $TiO_2$ from 2 ppm to 30 ppm, and the transmittance at a wavelength of 200 nm is less than 3%.

6. The glass of claim 1, wherein the glass has a total platinum content below 1.0 ppm.

7. The glass of claim 1, wherein the glass has a wave front deviation (peak to valley) of less than =0.1 mm.

8. The glass of claim 1, wherein the glass has a refractive index $n_d$ of from 1.450 to 1.580.

9. The glass of claim 1, wherein the glass comprises the following components in the indicated amounts (in mol %):

| Component | Content [mol %] |
|---|---|
| $SiO_2$ | 70 to 80 |
| $Al_2O_3$ | 0.5 to 4.5 |
| $Na_2O$ | 4 to 10 |
| $K_2O$ | 4 to 8 |
| MgO | 0 to 10 |
| $B_2O_3$ | 1.5 to 2.0 |
| $Li_2O$ | 0 to 2 |
| ZnO | 0 to 5 |
| CaO | 0 to 1 |
| BaO | 1.5 to 4 |
| $ZrO_2$ | 0 to 5 |
| $SnO_2$ | 0 to 3 |
| SrO | 0 to 4 |
| $F^-$ | 1 to 2 |
| $Cl^-$ | 0 to 1. |

10. The glass of claim 1, wherein the glass is thermally toughened or chemically toughened.

11. The glass of claim 10, wherein the glass has a compressive stress on at least one surface of at least 50 MPa.

12. A device, comprising:

a light source configured to output ultraviolet (UV) light; and a lamp cover covering the light source, the lamp cover comprising a glass having a transmittance at a wavelength of 220 nm of at least 30% and a transmittance at a wavelength of 200 nm of less than 4.0%, the glass having a total platinum content of less than 3.5 ppm, wherein the glass comprises the following components in the indicated amounts (in mol %):

| Component | Content [mol %] |
|---|---|
| $SiO_2$ | 70 to 80 |
| $Al_2O_3$ | 0.5 to 4.5 |
| $B_2O_3$ | 1.5 to 2.0 |
| $Li_2O$ | 0 to 2 |
| $Na_2O$ | 4 to 10 |
| $K_2O$ | 4 to 8 |
| CaO | 0 to 1 |
| SrO | 0 to 0.5 |
| BaO | 1.5 to 4 |
| $F^-$ | 0 to 2. |

13. The device of claim 12, wherein the glass has a transmittance of at least 75% at wavelengths of at least one of 260 nm, 280 nm or 310 nm.

14. The device of claim 12, wherein the glass has a transmittance of at least 40% at a wavelength of 220 nm.

15. The device of claim 12, wherein the glass comprises a total content of $Fe_2O_3$ from 0.5 ppm to 10 ppm.

16. The device of claim 15, wherein the glass has a content of $Fe_2O_3$ from 1 ppm to 10 ppm, a content of $TiO_2$ from 2 ppm to 30 ppm, and the transmittance at a wavelength of 200 nm is less than 3%.

17. The device of claim 12, wherein the glass has a total platinum content below 1.0 ppm.

18. The device of claim 12, wherein the glass has a wave front deviation (peak to valley) of less than +0.1 mm.

19. The device of claim 12, wherein the glass has a refractive index $n_d$ of from 1.450 to 1.580.

20. The device of claim 12, wherein the glass comprises the following components in the indicated amounts (in mol %):

| Component | Content [mol %] |
|---|---|
| $SiO_2$ | 70 to 80 |
| $Al_2O_3$ | 0.5 to 4.5 |
| $Na_2O$ | 4 to 10 |
| $K_2O$ | 4 to 8 |
| MgO | 0 to 10 |
| $B_2O_3$ | 1.5 to 2.0 |
| $Li_2O$ | 0 to 2 |
| ZnO | 0 to 5 |
| CaO | 0 to 1 |
| BaO | 1.5 to 4 |
| $ZrO_2$ | 0 to 5 |
| $SnO_2$ | 0 to 3 |
| SrO | 0 to 4 |
| $F^-$ | 1 to 2 |
| $Cl^-$ | 0 to 1. |

21. A sterilizer, comprising:

a light source configured to output ultraviolet (UV) light at a wavelength of 222 nm; and a lamp cover covering the light source, the lamp cover comprising a glass having a transmittance at a wavelength of 220 nm of at least 30% and a transmittance at a wavelength of 200 nm of less than 4.0%, the glass having a total platinum content of less than 3.5 ppm, wherein the glass comprises the following components in the indicated amounts (in mol %):

| Component | Content [mol %] |
|---|---|
| $SiO_2$ | 70 to 80 |
| $Al_2O_3$ | 0.5 to 4.5 |
| $B_2O_3$ | 1.5 to 2.0 |
| $Li_2O$ | 0 to 2 |
| $Na_2O$ | 4 to 10 |
| $K_2O$ | 4 to 8 |
| CaO | 0 to 1 |
| SrO | 0 to 0.5 |
| BaO | 1.5 to 4 |
| $F^-$ | 0 to 2. |

22. The sterilizer of claim 21, wherein the UV light output by the light source is effective to eradicate pathogens after passing through the lamp cover.

\* \* \* \* \*